(12) United States Patent
Masotti et al.

(10) Patent No.: US 6,169,917 B1
(45) Date of Patent: Jan. 2, 2001

(54) METHOD AND DEVICE FOR RECONSTRUCTING THREE-DIMENSIONAL IMAGES OF BLOOD VESSELS, PARTICULARLY CORONARY ARTERIES, OR OTHER THREE-DIMENSIONAL STRUCTURES

(76) Inventors: Leonardo Masotti, Via Bolognese, 81, 50019 Sesto F.NO, Florence; Riccardo Pini, Via Delle Porte Nvove, 27, 50144 Firenze; Francesco Buzzigoli, Via XXV Aprile 37, 50019, Sesto F.No., Florence; Ada Fort, Via Cacuni 15, 50141 Florence, all of (IT)

( * ) Notice: Under 35 U.S.C. 154(b), the term of this patent shall be extended for 0 days.

(21) Appl. No.: 09/222,099

(22) Filed: Dec. 29, 1998

(30) Foreign Application Priority Data

Dec. 30, 1997 (IT) ................................................. FI97A0288

(51) Int. Cl.[7] ........................................................ A61B 5/00
(52) U.S. Cl. .............................................................. 600/407
(58) Field of Search ................................... 600/407, 425, 600/426, 429, 436

(56) References Cited

U.S. PATENT DOCUMENTS

| 5,699,799 | * | 12/1997 | Xu et al. | 600/425 |
| 5,891,030 | * | 8/1999 | Johnson et al. | 600/407 |

* cited by examiner

Primary Examiner—William E. Kamm
(74) Attorney, Agent, or Firm—McGlew and Tuttle, P.C.

(57) ABSTRACT

A description is given of a device and a method for reconstructing the three-dimensional structure of blood vessels or other structures. The method comprises the stages of: obtaining at least three images of the blood vessels to be reconstructed, each of said images showing reference points which permit the determination of a matrix (T) which describes the geometric projections associated with each image; identifying, by means of said three images, a starting point for the tracing of a center line of a blood vessel; tracking the center line of the blood vessel to an end point; determining the cross-sectional dimension of said blood vessel at a plurality of points of the center line; reconstructing the three-dimensional image of the blood vessel from said cross-sectional dimensions and said center line.

17 Claims, 12 Drawing Sheets

| # | D1 | | D2 | D3 | |
|---|---|---|---|---|---|
| | pixel | (mm) | pixel | pixel | (mm) |
| 1 | 14.58 | (1.75) | 15.4 | 15.09 | (1.81) |
| 2 | 16.09 | (1.93) | 17.63 | 17.78 | (2.13) |
| 3 | 15.6 | (1.87) | 17.78 | 17.44 | (2.09) |
| 4 | 16.14 | (1.94) | 19.31 | 17.5 | (2.1) |
| 5 | 16.45 | (1.97) | 19.33 | 16.78 | (2.01) |
| 6 | 15.81 | (1.9) | 19.3 | 17 | (2.04) |
| 7 | 16.27 | (1.95) | 20.7 | 16.2 | (1.94) |
| 8 | 16.55 | (1.99) | 23.17 | 17.2 | (2.06) |
| 9 | 16.55 | (1.99) | 22.67 | 16.29 | (1.96) |
| 10 | 16.45 | (1.97) | 23.33 | 16.75 | (2.01) |
| 11 | 16.42 | (1.97) | 23 | 15.8 | (1.90) |
| 12 | 16.58 | (1.99) | 24.91 | 16.5 | (1.98) |
| 13 | 17 | (2.04) | 20 | 14.17 | (1.70) |
| 14 | 17.5 | (2.1) | 21.43 | 13 | (1.56) |
| 15 | 13.29 | (1.6) | 17.67 | 9.25 | (1.11) |
| 16 | 8.63 | (1.04) | 20.5 | 9.71 | (1.17) |
| 17 | 9.11 | (1.09) | 17.22 | 9.57 | (1.15) |
| 18 | 9.7 | (1.16) | 18.5 | 11.14 | (1.34) |
| 19 | 11.89 | (1.43) | 19.25 | 14.6 | (1.75) |
| 20 | 16.54 | (1.99) | 21.1 | 17 | (2.04) |
| 21 | 16.58 | (1.99) | 21.7 | 17.14 | (2.06) |
| 22 | 16.67 | (2.00) | 21.73 | 17.5 | (2.10) |
| 23 | 16.55 | (1.99) | 24.36 | 17.56 | (2.11) |
| 24 | 16.42 | (1.97) | 22.5 | 17.88 | (2.15) |
| 25 | 16.25 | (1.95) | 21.64 | 17.29 | (2.08) |
| 26 | 16.37 | (1.96) | 20.3 | 17.83 | (2.14) |
| 27 | 16.18 | (1.94) | 20.5 | 18.13 | (2.18) |
| 28 | 16.15 | (1.94) | 19.5 | 18.17 | (2.18) |
| 29 | 15.72 | (1.89) | 17.11 | 17.17 | (2.06) |
| 30 | 16.62 | (1.99) | 17.6 | 17.14 | (2.06) |
| 31 | 16.4 | (1.97) | 15.43 | 13 | (1.56) |
| 32 | 13.38 | (1.61) | 17.75 | 12 | (1.44) |
| 33 | 10.29 | (1.24) | 17.33 | 13 | (1.56) |
| 34 | 7.7 | (0.93) | 19 | 5.25 | (8.19) |
| 35 | 2.75 | (0.33) | 19.9 | 3 | (0.36) |

METHOD AND DEVICE FOR RECONSTRUCTING THREE-DIMENSIONAL IMAGES OF BLOOD VESSELS, PARTICULARLY CORONARY ARTERIES, OR OTHER THREE-DIMENSIONAL STRUCTURES

DESCRIPTION

The present invention relates to a method and a device capable of reconstructing the three-dimensional structure of complex blood vessels, particularly the structure of the coronary arteries. The method and the device are also suitable for reconstructing three-dimensional structures other than the structures of blood vessels. In the following text, therefore, unless specified otherwise, the term "vessel" denotes any elongate three-dimensional structure whose three-dimensional image is to be reconstructed from two-dimensional images.

Since 1959, the date of production of the first catheter which made it possible to reach the emergence of the system of coronary arteries, to inject the contrast medium into them and thus to permit the visualization of the epicardial arterial vessels by using X-rays, there has been a constant improvement of the angiographic images. At the present time, examinations carried out with an angiography instrument called a coronary angiograph are widely used.

However, less progress has been made in the identification of an objective and accurate method for analyzing these images. The evaluation of the relevant clinical parameters from angiographic photograms continues to be affected by serious errors of interpretation due to the loss of information associated with the projection of a three-dimensional object on a plane. It is therefore important to integrate the data obtained from a plurality of images and to reconstruct the three-dimensional structure of the coronary arteries.

The object of the present invention is to provide a device and a method capable of reconstructing the three-dimensional structure of the coronary arteries, or of other systems of vessels or even of other three-dimensional structures, by means of the analysis of three or more angiographic images, possibly acquired at different times.

Essentially, the system consists of a coronary angiograph, a reference object integral with the patient, enabling the geometric characterization of the coronary angiograph to be carried out, and an algorithm which can provide the 3D reconstruction of the tree of the coronary vessels on the basis of the analysis of each image and from the geometric characteristics of the coronary angiograph itself. Reference will be made in the following text to the analysis of the coronary arteries, but it should be understood that the same system can also be used for examining other structures of blood vessels, or structures in other parts of the human or animal body, or even structures of other types, such as mechanical structures, objects of art or archeological finds to be restored, or similar.

The proposed instrument carries out the reconstruction in a semi-automatic way, and enables the most appropriate projections for the diagnostic examination to be identified from the reconstructed three-dimensional structure. Another object of the patent, therefore, is the procedure of automatic selection of the exposures which contribute to the acquisition of images with a high information content.

The method according to the invention and the corresponding device are specified in the attached claims.

The invention will be more clearly understood from the description and the attached drawing, which shows a non-restrictive practical embodiment of the invention. In the drawing.

FIG. 12A shows the coronary angiograph of FIG. 12 in a different arrangement;

The present invention makes use of the images produced by a coronary angiograph. The structure of a coronary angiograph is shown schematically in FIG. 1. The coronary angiograph essentially consists of at least one X-ray source indicated by the number 1, held on a support 3, and an image intensifier 5, both devices being arranged on a moving arm 6, and made to be located on opposite sides of the chest of the patient who is lying on a bed 7. The image formed on the image intensifier is stored either in the form of film (35 mm photographic film) or in a digitized form which is acquired by a digital processing system. In some instruments ("biplane coronary angiographs") two X-ray sources and two image intensifiers are provided, to obtain two images simultaneously at two different angles.

The angiographic images used for the reconstruction may be obtained by using a coronary angiograph with a single X-ray tube, or by means of a biplane coronary angiograph, in other words one having two tubes and two intensifiers and capable of acquiring two images simultaneously. In all cases, the three images used in the reconstruction algorithm described below must represent the same instant of the cardiac cycle. This may be achieved by a posteriori analysis of the filmed images acquired during the examination, or by providing a system, based for example on a reading of the ECG, for synchronizing the instrument with the cardiac cycle.

Figure 12:
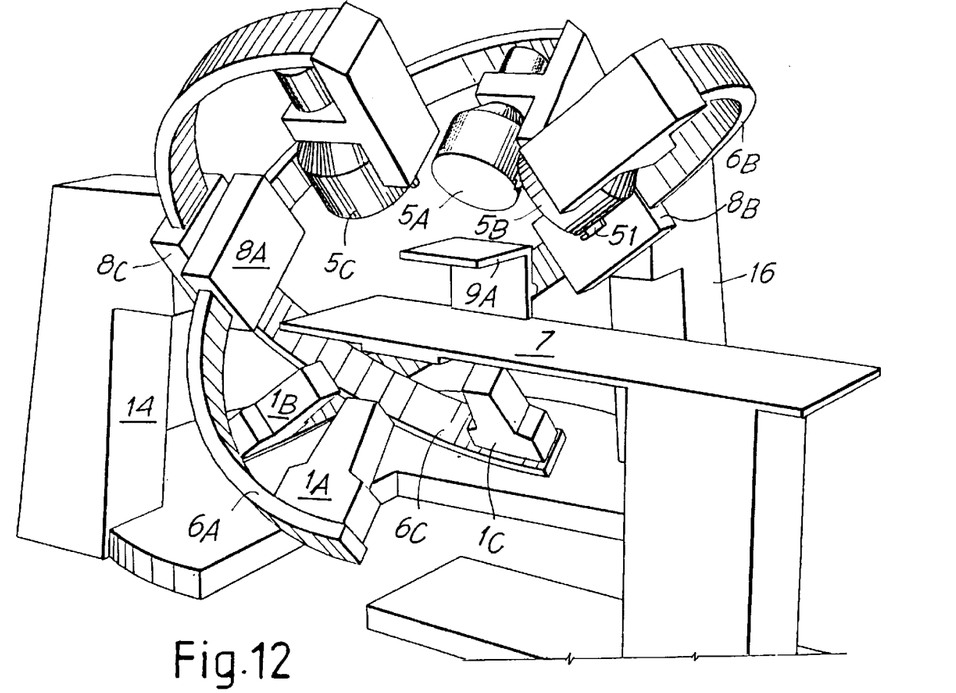
FIG. 12 is a perspective view of a three-arm coronary angiograph, with three X-ray sources and three image intensifiers.

The reconstruction system may, however, also be based on a newly designed coronary angiograph which provides at least three X-ray sources and three intensifiers and is capable of supplying simultaneously the three synchronized images required for the reconstruction, this instrument being described below in greater detail with reference to FIGS. 12, 12A and 13.

THEORY

The angiographic images can be treated as perspective projections.

Mathematically, a generic perspective projection can be described by a 4×4 matrix, according to the following equation:

$$[x\ y\ z\ 1]T' = [X\ Y\ 0\ H] \quad \text{Eq. 1}$$

The three-dimensional point whose coordinates are (x y z) is represented in homogeneous coordinates by [x y z 1] and is projected to the point [X Y 0 H], in homogeneous coordinates, which corresponds to the point whose physical coordinates are (X/H, Y/H, 0)=(x' y' 0), where the plane Z=0 is selected as the projection plane.

The equations associated with the transformation are therefore:

$$t_{11}x + t_{21}y + t_{31}z + t_{41} = Hx'$$

$$t_{12}x + t_{22}y + t_{32}z + t_{42} = Hy'$$

$$t_{13}x + t_{23}y + t_{33}z + t_{43} = H \quad \text{Eq. 2}$$

Substituting the parameter H, found by means of the last equation, in the first two, we obtain:

$$(t_{11} - t_{14}x')x + (t_{21} - t_{24}x')y + (t_{31} - t_{34}x')z + (t_{41} - t_{44}x') = 0$$

$$(t_{12} - t_{14}x')x + (t_{22} - t_{24}x')y + (t_{32} - t_{34}x')z + (t_{42} - t_{44}x') = 0 \quad \text{Eq. 3}$$

This pair of equations can be used in different conditions of application:

When the transformation T and the coordinates (x, y, z) of the three-dimensional point are known, the coordinates x' and y' of the point's projection can be found.

When two transformations, $T_1 = [t^1_{ij}]$ and $T_2 = [t^2_{ij}]$, and the two-dimensional coordinates $(x'_1, y'_1)$ and $(x'_2, y'_2)$ of the two points obtained by projecting a three-dimensional point on two projection planes are known, it is possible to write the two equations (3) for both points, and we find that:

$$AX = B$$

By solving the over-dimensioned system in Eq. 4 (four equations with three unknown quantities) the three-dimensional coordinates (x, y, z) of the projected point can be found.

$$A = \begin{bmatrix} (t^1_{11} - t^1_{14}x'_1) & (t^1_{21} - t^1_{24}x'_1) & (t^1_{31} - t^1_{34}x'_1) & (t^1_{41} - t^1_{44}x'_1) \\ (t^1_{12} - t^1_{14}x'_1) & (t^1_{22} - t^1_{24}x'_1) & (t^1_{32} - t^1_{34}x'_1) & (t^1_{42} - t^1_{44}x'_1) \\ (t^2_{11} - t^2_{14}x'_2) & (t^2_{21} - t^2_{24}x'_2) & (t^2_{31} - t^2_{34}x'_2) & (t^2_{41} - t^2_{44}x'_2) \\ (t^2_{12} - t^2_{14}x'_2) & (t^2_{22} - t^2_{24}x'_2) & (t^2_{32} - t^2_{34}x'_2) & (t^2_{42} - t^2_{44}x'_2) \end{bmatrix} \quad \text{Eq. 4}$$

$$X^T = [x\ y\ z]$$

$$B^T = [t_{44}^1 x'_1 - t_{41}^1\ \ t_{44}^1 y'_1 - t_{42}^1\ \ t_{44}^2 x'_2 - t_{41}^2\ \ t_{44}^2 y'_2 - t_{42}^2]$$

On the other hand, when the transformation T is unknown, but the 3D coordinates of at least six points are known, it is possible to write the two equations (3) for all the points, thus obtaining a system of twelve equations with eleven unknown quantities, given that $t_{44}=1$:

$$A = \begin{bmatrix} x_1 & 0 & -x_1 x'_1 & y_1 & 0 & -y_1 x'_1 & z_1 & 0 & -z_1 x'_1 & 1 & 0 \\ 0 & x_1 & -x_1 y'_1 & 0 & y_1 & -y_1 y'_1 & 0 & z_1 & -z_1 y'_1 & 0 & 1 \\ x_2 & 0 & -x_2 x'_2 & y_2 & 0 & -y_2 x'_2 & z_2 & 0 & -z_2 x'_2 & 1 & 0 \\ 0 & x_2 & -x_2 y'_2 & 0 & y_2 & -y_2 y'_2 & 0 & z_2 & -z_2 y'_2 & 0 & 1 \\ x_3 & 0 & -x_3 x'_3 & y_3 & 0 & -y_3 x'_3 & z_3 & 0 & -z_3 x'_3 & 1 & 0 \\ 0 & x_3 & -x_3 y'_3 & 0 & y_3 & -y_3 y'_3 & 0 & z_3 & -z_3 y'_3 & 0 & 1 \\ x_4 & 0 & -x_4 x'_4 & y_4 & 0 & -y_4 x'_4 & z_4 & 0 & -z_4 x'_4 & 1 & 0 \\ 0 & x_4 & -x_4 y'_4 & 0 & y_4 & -y_4 y'_4 & 0 & z_4 & -z_4 y'_4 & 0 & 1 \\ x_5 & 0 & -x_5 x'_5 & y_5 & 0 & -y_5 x'_5 & z_5 & 0 & -z_5 x'_5 & 1 & 0 \\ 0 & x_5 & -x_5 y'_5 & 0 & y_5 & -y_5 y'_5 & 0 & z_5 & -z_5 y'_5 & 0 & 1 \\ x_6 & 0 & -x_6 x'_6 & y_6 & 0 & -y_6 x'_6 & z_6 & 0 & -z_6 x'_6 & 1 & 0 \\ 0 & x_6 & -x_6 y'_6 & 0 & y_6 & -y_6 y'_6 & 0 & z_6 & -z_6 y'_6 & 0 & 1 \end{bmatrix} \quad \text{Eq. 5}$$

$$X^T = [t_{11}\ t_{12}\ t_{14}\ t_{21}\ t_{22}\ t_{24}\ t_{31}\ t_{32}\ t_{34}\ t_{41}\ t_{42}]$$

$$B^T = [t_{44}x'_1\ t_{44}y'_1\ t_{44}x'_2\ t_{44}y'_2\ t_{44}x'_3\ t_{44}y'_3\ t_{44}x'_4\ t_{44}y'_4\ t_{44}x'_5\ t_{44}y'_5\ t_{44}x'_6\ t_{44}y'_6]$$

The system in Equation 5 can be solved if the equations are independent, in other ways provided that the six points satisfy the following conditions: not more than three points can be colinear and not more than four points can be coplanar.

From this brief summary of the theory of perspective projections it follows that there are at least two angiographic images (projections) and that, if the matrices T which describe them are known, it is possible to find the three-dimensional coordinates of the point which has generated them.

In order to obtain the three-dimensional reconstruction of the tree of the coronary arteries, therefore, it is necessary to solve the following problems:

The problem of the determination of the perspective transformations associated with each angiographic image. It is necessary to determine the matrix T which describes the geometrical projections associated with each angiographic image.

The problem of correspondence. It is necessary to identify, in each image, the points which correspond to the projections of the same point belonging to the three-dimensional object which is to be reconstructed.

The problem of three-dimensional reconstruction. When the problem of correspondence has been solved, it is necessary to determine some three-dimensional points belonging to the tree of the coronary arteries and to interpolate them by means of a suitable three-dimensional model.

Figure 1:
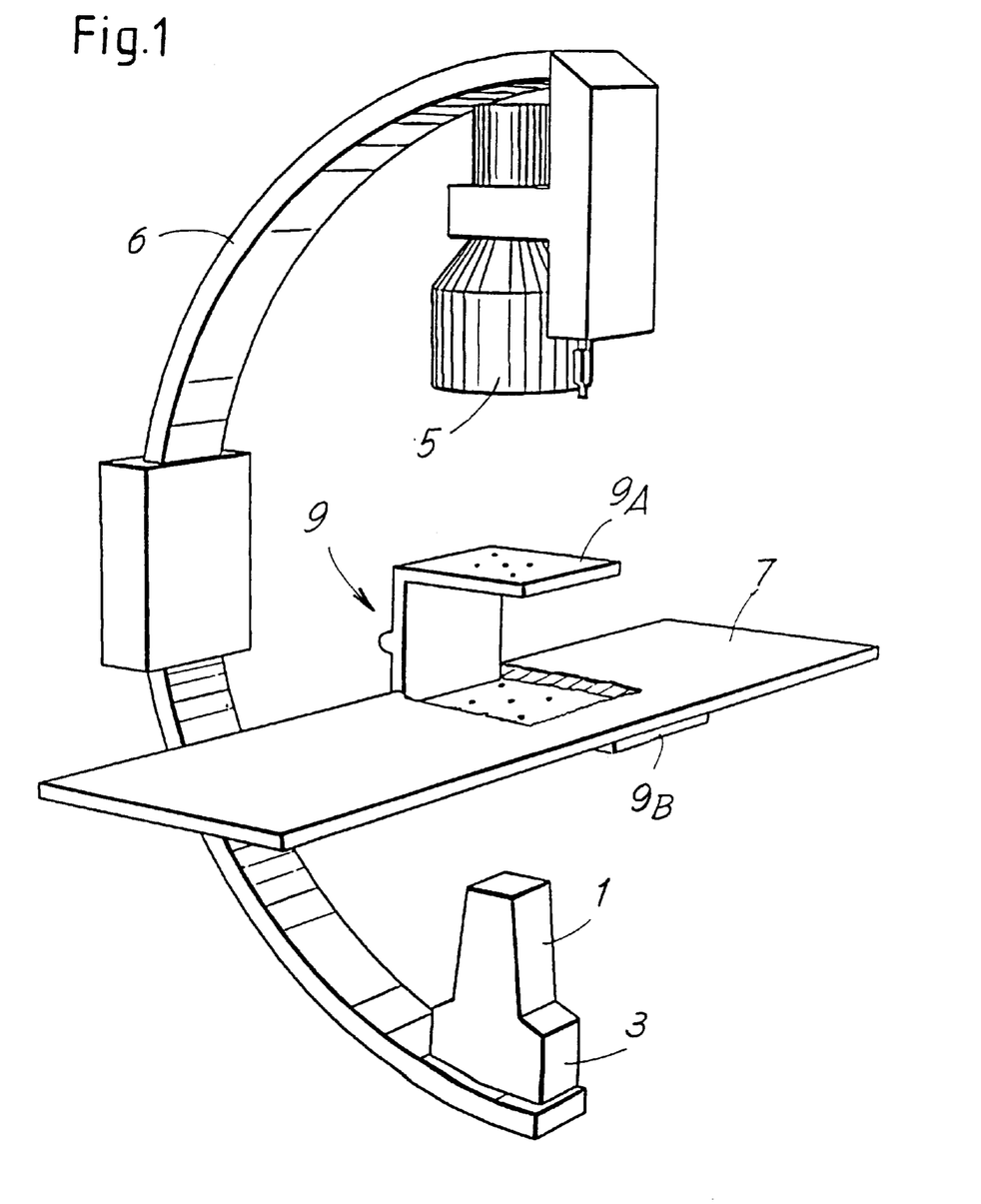
FIG. 1 is a perspective view of a single-arm coronary angiograph, with a source and an image intensifier.

Determination of the perspective transformations associated with each angiographic image This problem is solved by using a reference object which must be integral with the patient during the examination. In FIG. 1, this object, indicated in a general way by the number 9 comprises two planes 9A, 9B which are arranged under and above the patient. Certain points which are opaque to the radiation used by the coronary angiograph, for example lead or similar elements, are placed on the two planes 9A, 9B. In practice, the object 9 must contain at least six points with known three-dimensional coordinates which satisfy the aforementioned conditions (not more than three colinear points, not more than four coplanar points). By identifying the projection of these points on the angiographic images, it is possible, by solving the system shown at (5), to calculate the matrices T associated with the perspective transformations. The reference points must be identifiable in the images whenever one of the arms 6 constituting the coronary angiographic instrument moves with respect to the patient (in other words, when the perspective projection associated with the angiographic image is changed). Their presence is necessary in only some of the photograms which constitute the filmed images for the individual projections. It is therefore possible to provide a reference object which loses its radiopacity or which departs from the imaging area on completion of the acquisition of the images required for the determination of the corresponding perspective transformation matrices used for the reconstruction.

Figure 2:
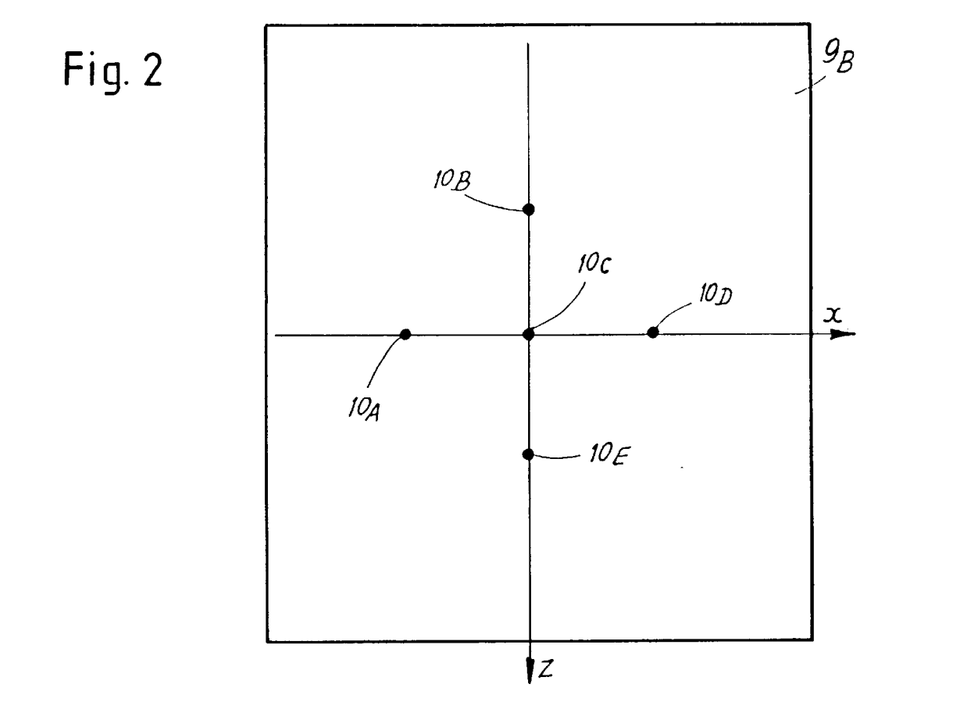
FIGS. 2 and 3 show the positions of the radiopaque objects on the two planes associated with the coronary angiograph shown in FIG. 1.
Figure 3:
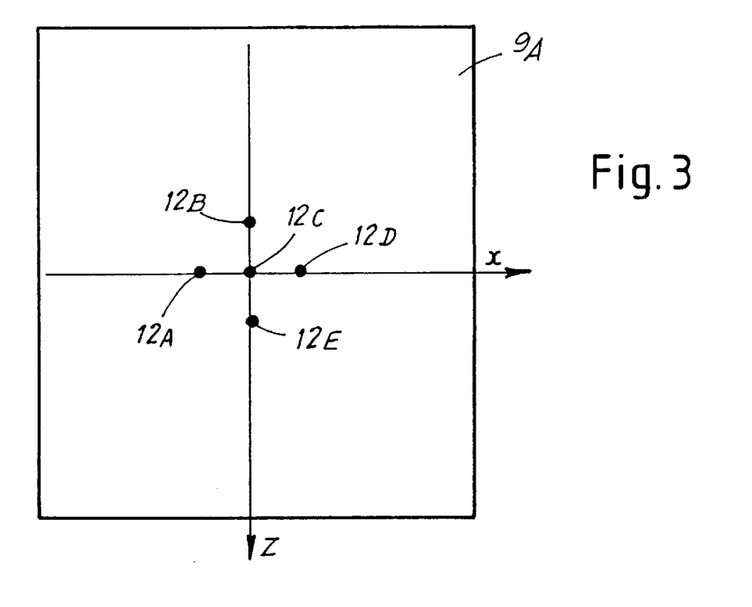

In the example shown in FIG. 1, a panel of transparent material (Plexiglas®), constituting the plane 9B, is fixed to the bed 7 and is positioned under the patient's chest. The upper panel 9A, parallel to the lower panel, is located above the patient's chest during the examination; the upper plate can be rotated outwardly from the bed by means of a hinge, to enable the patient to lie down. The reference objects are lead pellets, five on the upper plane and five on the lower plane. FIGS. 2 and 3 show plan views of the two panels 9A, 9B with a possible arrangement of the five radiopaque points, indicated by 10A–10E and 12A–12E.

The radiopaque objects can be differentiated in terms of shape. The reference points can be identified manually or automatically (by shape recognition) in the angiographic images.

Correspondence

An analysis of the angiographic images must be carried out initially to trace the tree of the coronary arteries, in other words to identify the profiles of the central lines of the arteries and the diameters.

The tracings obtained by the aforesaid analysis represent a set of points of projection of the three-dimensional object. By using an automatic method to establish a correspondence between the various two-dimensional points belonging to different images, it is possible to reconstruct the three-dimensional structure.

It has been asserted that, theoretically, two perspective projections found in different lines of sight are sufficient to obtain a 3D reconstruction of an object.

However, the perspective reconstruction of the tree of the coronary arteries is impeded by a number of problems, including the ambiguity arising from the superimposition of vessels.

In order to partially overcome this problem and to simplify the solution of the correspondence problem, the three-dimensional reconstruction is obtained by means of the analysis of at least three angiographic images.

When the number of images is increased, the probability of being able to resolve the ambiguities increases, and it is possible to use an algorithm which determines the correspondence between the points in an automatic way.

Figure 4:
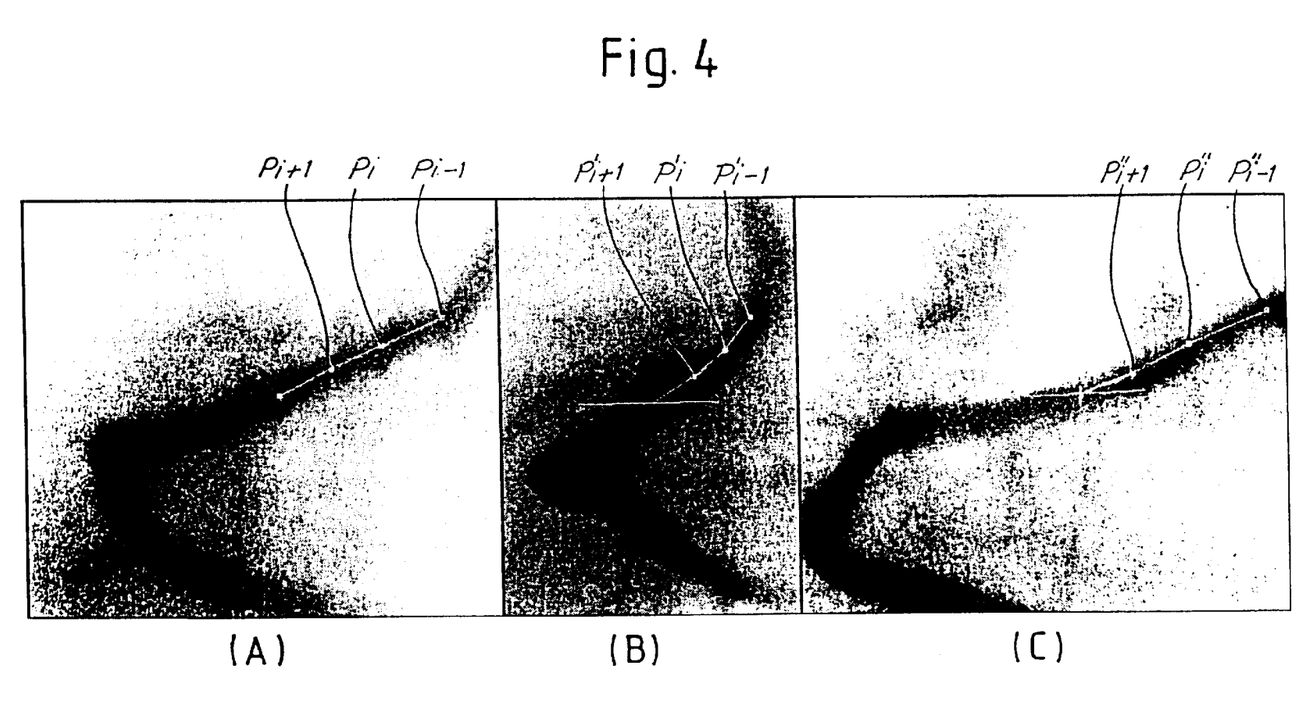
FIG. 4 shows three images obtained by the coronary angiograph at three different angles.

The center line of the vessel is traced by starting with one of the three images used, described in the following text as the "principal view". The procedure followed is described with reference to FIGS. 4A, 4B, 4C, which show schematically the three views of the same portion of the tree of coronary arteries. FIG. 4A shows the principal view, while FIGS. 4B and 4C represent a second and a third view respectively.

The reconstruction is obtained by using a semi-automatic tracking algorithm, which must be started by manually determining the starting point of the vessel. The projection of this point is selected manually on the principal view. For this purpose, the principal view is projected on a monitor of an electronic computer, and a suitable pointing device, such as a mouse, is used to define the starting point of the tracing. In FIG. 4A, the starting point of the tracing of the center line of the vessel is indicated by $P_{i-1}$. To start tracing the vessel in space, the projection of the starting point $P_{i-1}$ must be identified, on another view if necessary. On the second image (FIG. 4B), a point, indicated by $P'_{i-1}$, which represents the approximation of the projection of the three-dimensional point $P_{i-1}$ on the second view of the portion of vessel, is selected by means of the mouse.

The three-dimensional point which can be re-projected on the third view (FIG. 4C) is reconstructed on the basis of these two points. It is therefore possible to select as the projection of the starting point $P'_{i-1}$ on the second image (FIG. 4B) the point which, when re-projected on the third image (FIG. 4C), actually lies on the center line of the projection of the vessel in question on the third image, indicated by $P''_{i-1}$.

In addition to the starting point $P_{i-1}$, the initial direction of the vessel, represented by the vector $d_i = P_i - P_{i-1}$ in FIG. 4A, must be identified in the principal view. The tracking algorithm proceeds in an iterative way, identifying in each step a new segment of vessel whose length is proportional to the actual radius, evaluating the probability that the vessel proceeds in a given direction and selecting the most probable direction. This probability is obtained by calculating the mean gray level contained in a rectangular mask which is rotated about the point belonging to the center line of the vessel and identified in the preceding step. The dimensions of the mask are selected on the basis of the estimated dimensions of the vessel, estimated in the preceding step.

Figures 5, 6:
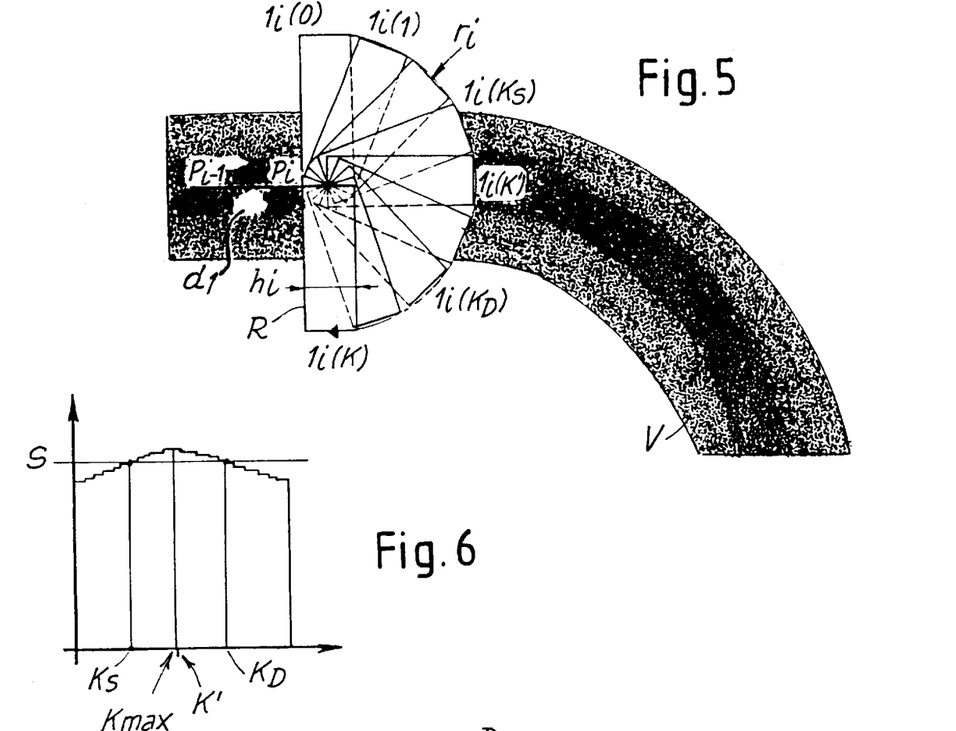
FIGS. 5, 6 and 7 show diagrams for the description of the vessel tracking algorithm.

The operation of the tracking algorithm is described in greater detail with reference to FIGS. 5 and 6, where FIG. 5 represents schematically a portion of vessel V in the principal view, for which $P_{i-1}$ indicates the starting point set manually to start the algorithm, and $P_i$ indicates the second point which identifies the vector $d_i$ (initial direction of the vessel). The algorithm is developed as follows:

1) when the starting point $P_{i-1}$ and the initial reference direction have been set by means of the vector $d_i$, the initial scanning radius $r_i$ and the initial thickness $h_i$ are determined:

$$r_i = |d_i|; \quad h_i = |d_i|/2$$

2) a geometrical figure R, which in the illustrated example is a rectangle with sides equal to $h_i$ and $r_i$, is constructed (see FIG. 6) (it should be understood that a different geometrical figure, such as an ellipse, could also be constructed);

3) the center of one of the short sides of the rectangle R is placed at the point $P_i$, in other words at the terminal point of the vector $d_i$;

4) the rectangle R is rotated through 180° about the center of rotation represented by the point $P_i$;

5) whenever the raster scanning of this generates a new area, the underlying gray levels belonging to the angiographic image are determined and the corresponding mean value and angle of rotation ($\beta_i[k]$) are stored, generating a vector $\beta_i$;

6) a vector $l_i$, containing the means of the gray levels found for each direction examined, is generated;

7) the vector $l_i$ is processed as follows:

7a) the maximum value $l_{i\,max}$ and the mean value $l_{i\,mean}$ of the values of $l_i$ are calculated;

7b) a threshold $s_i$ proportional to the values $l_{i\,max}$ and $l_{i\,mean}$ defined above is initialized;

7c) starting from the position of the maximum value $k_{max}$, the directions $k_s$ and $k_d$ relating to the mean values which are found to be immediately below the set threshold $s_i$, on the left hand and on the right hand respectively, are determined (see FIG. 6);

7d) a direction k' is calculated as the mean value between $k_s$ and $k_d$;

8) the angle associated with the position k' of the vector ($\beta_i[k]$) represents the desired direction of the center line of the vessel;

9) if the difference between $l_{i\,max}$ and $l_{i\,mean}$ is equal to or greater than a certain value which may be set, for example 1–3 pixels, the new variables $P_{i+1}$, $d_{i+1}$, $h_{i+1}$, $r_{i+1}$ are initialized, and the procedure is restarted from point 2); otherwise, the automatic tracking is interrupted and the operator intervenes to recommence the procedure by assigning a direction by observation of the three images, for example by the procedure described for the starting point $P_i$, since an insufficiently marked difference between $l_{i\,max}$ and $l_{i\,mean}$ indicates a situation in which the image has insufficient contrast for the continuation of automatic tracking, or that the end of the coronary vessel has been reached.

Experiments showed that it was necessary to introduce another check immediately after the identification of the indices $k_s$ and $k_d$ calculated as described above: if the difference $|k_s - k_d|$ on the i-th iteration is less than a predetermined fraction of that calculated during the preceding iteration, the values which have been found are rejected, and the search for the next relative maximum is continued by continuing the scanning of the vector l.

A first estimate of the size of the radius for the next iteration is given by:

$$r_{i+1} = |k_{is} - k_{id}| * 1.5$$

where $k_{is}$ and $k_{id}$ are the values of $k_s$ and $k_d$ estimated in the i-th step.

Before being used, this new value is mediated with the three values of the preceding segments; in this way the algorithm is made less sensitive to sharp variations of contrast present inside the coronary profile:

$$r_{i+1} = (r_{i-2} + r_{i-1} + r_i + r_{i+1})/4$$

In the first iteration, therefore, the vector which keeps these values stored must have all the elements equal to the initial radius: whenever the next segment is determined, the first value of the vector is eliminated, a shift of one cell is executed and the new radius is stored in the last cell.

When the radius for the step i+1 has been calculated, the new dimension $h_{i+1}$ of the rectangle is initialized:

$$h_{i+1} = |r_{i+1}|/2$$

Figure 7:
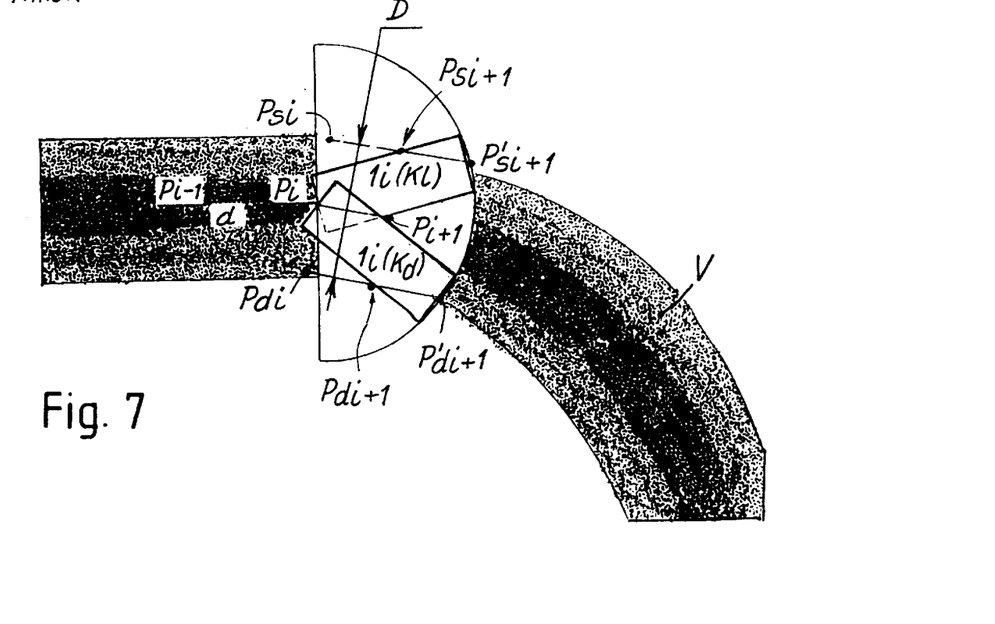

The algorithm described above may also enable the diameter of the vessel under examination to be estimated, by the procedure which will now be described with reference to FIG. 7. In every i-th step, the points $P'_{si+1}$ and $P'_{di-1}$ are determined (see FIG. 7), corresponding to the directions relating to the indices $k_{si}$ and $k_{di}$. From these points, the points $P_{si+1}$ and $P_{di+1}$ are calculated by simple linear interpolation with the points $P_{si}$ and $P_{di}$ generated by the preceding pass. The diameter D of the vessel in the i-th section is then estimated as the distance between the points $P_{si+1}$ and $P_{di+1}$:

$$D = \|P_{si+1} P_{di+1}\|$$

In each step of the algorithm, therefore, an increment of the center line of the vessel is provided, and one of the two ends $P_i$ (see FIG. 4A) represents a new two-dimensional point (projection on the principal view of a 3D point lying on the center line of the vessel). To obtain a similar increment of the center line of the reconstructed 3D vessel, it is necessary to identify the corresponding point $P'_i$ (or $P''_i$) on at least one of the other two views.

Figure 8:
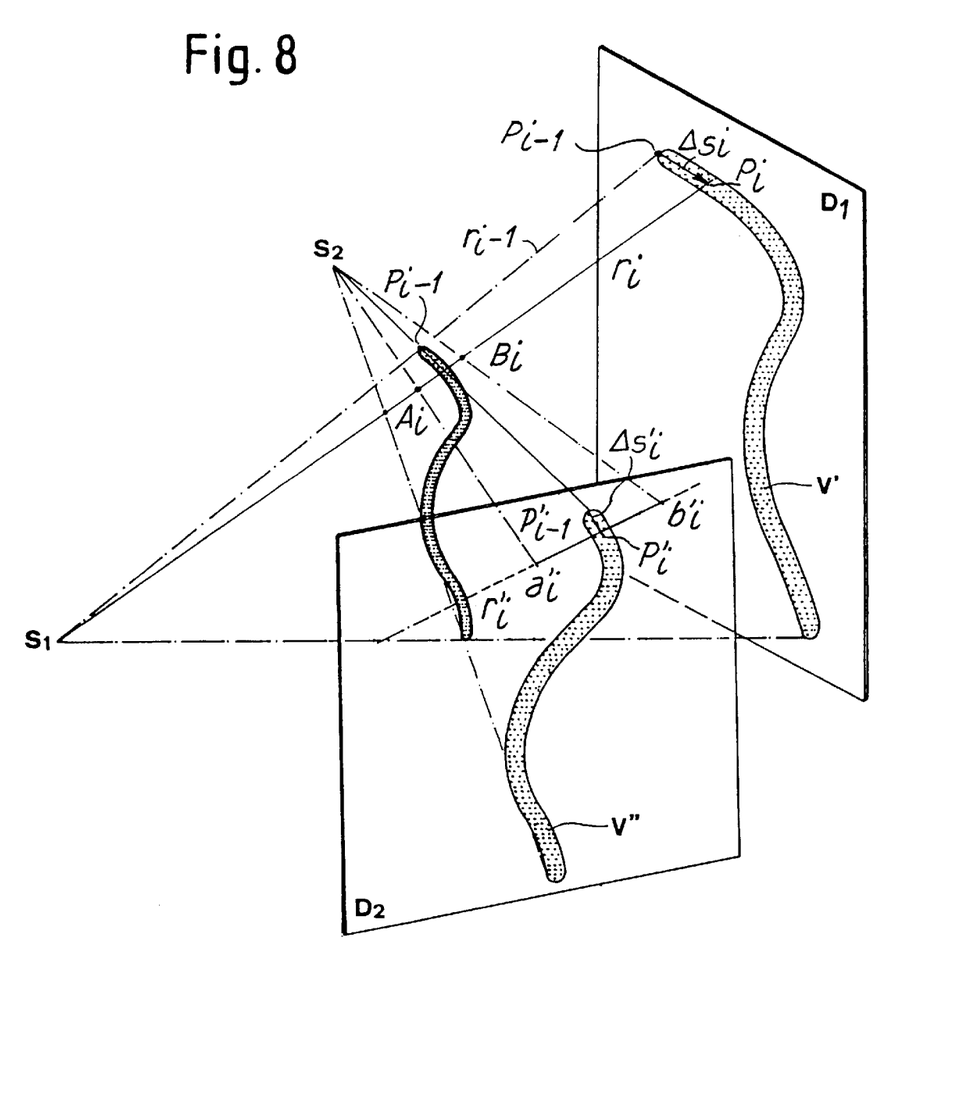
FIG. 8 is an illustrative diagram for the determination of the points of the center line of a vessel in various views.

The algorithm below, described with reference to FIG. 8, was developed for this purpose. In said figure, S1 and S2 indicate two sources of the angiograph, V indicates the vessel, D1 and D2 indicate the two planes of projection of two of the images of the vessel V (for example the principal view and the second view) generated by the sources S1 and S2, and V' and V'' indicate the images projected on the planes D1 and D2 by the sources S1 and S2.

By substituting the coordinates of the point $P_i$ in the equations (3) we obtain a straight line departing from the source S1 and passing through the point $P_i$ (projection of the real point of the vessel on the first image) and through the three-dimensional point which has generated it. By re-projecting this straight line (or a segment of it) on one of the other two views, on the plane D2 for example, we obtain a segment which passes through the projected artery profile present in the image (FIG. 8). $P'_i$ is the intersection of the segment thus obtained with the center line of the projection of the vessel on this image. $P'_i$ can be identified by analyzing the luminosity profile which is obtained by sampling the gray levels of the image in this segment. The center line of the vessel will be associated with the area of minimum luminosity. The procedure can be repeated for the second and third view. For the 3D reconstruction, use will be made of the one of the two points thus identified which lies on the image with which the greatest amount of information is associated, in other words on the view associated with the projection plane which is most nearly parallel to (in other words, least inclined with respect to) the segment of the axis of the vessel which is currently analyzed.

When the center line has been identified, there is a transition to the recognition of the thicknesses of the arterial vessels. A first estimate of the diameter can be obtained by the procedure described previously.

Figure 9:
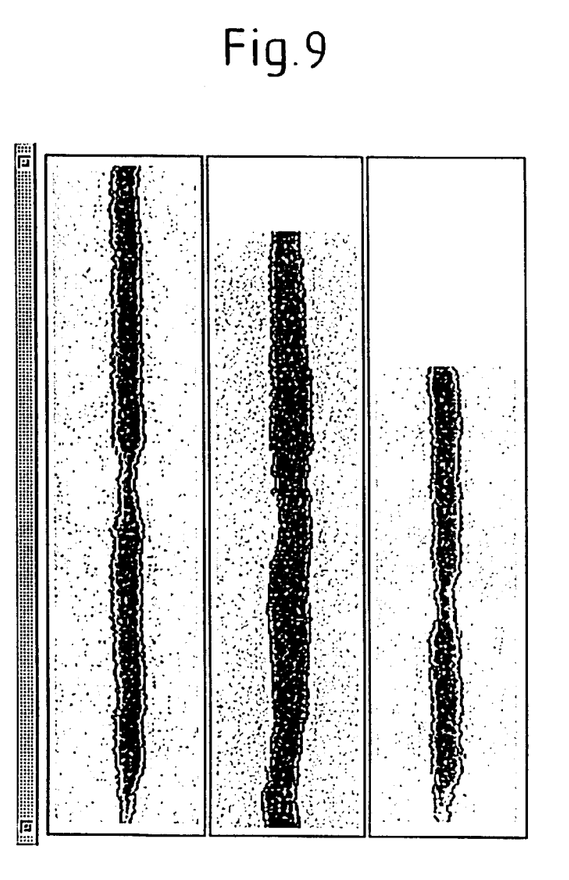
FIGS. 9 and 10 show the results of the determination of the transverse dimension of the vessels.
Figure 10:
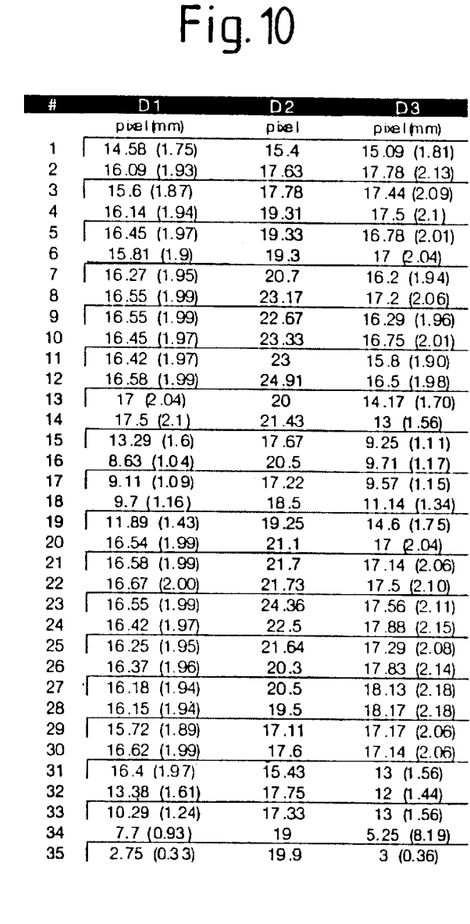

A more precise semi-automatic procedure is described with reference to FIGS. 9 and 10. This operation is carried out as a preliminary step, providing the operator with a simultaneous representation of three profiles obtained on the three views by means of a known algorithm which straightens the profiles. The program then proceeds to extract the contours for each segment belonging to the center lines, and stores the calculated values. FIG. 9 shows the three views of the straightened vessel, while FIG. 10 shows the table of the values in pixels and millimeters of the thicknesses measured in the three views. The thicknesses are also corrected by means of a function which allows for the three-dimensional position of the vessel segment, in other words in order to correct the variation of dimensions in the three images caused by the different distances between the vessel, the sources and the projection planes. The segments located in the portion of space not containing the source (more remote) are therefore weighted with values of more than unity with respect to the plane passing from the origin and perpendicular to the source of emission, while those located in the half-space containing the source (closer) are weighted with values of less than unity. Of the three views, the two which are found to be most nearly parallel to the vessel are selected, and for these the values of the thicknesses measured in the image are accepted for each section. The section of the vessel is determined as a circular section having a diameter equal to the mean of the two measured thicknesses, or as an elliptical section whose axes have dimensions equal to the measured thicknesses.

Figure 11:
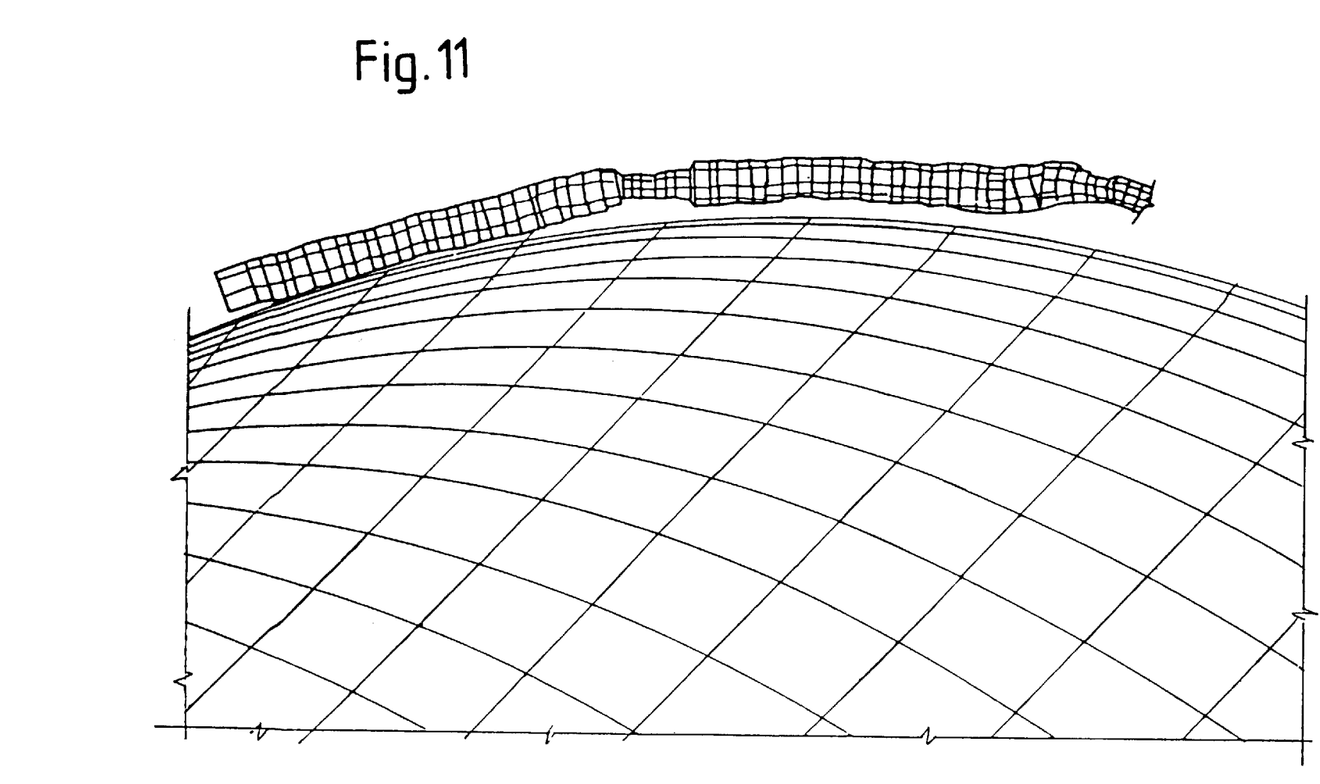
FIG. 11 shows schematically the reconstruction of a vessel as a set of truncated pyramidal sections from the data shown in FIGS. 9 and 10.

The 3D model which is generated consists of a set of truncated cones with circular bases (FIG. 11) which are positioned with their axes lying on the corresponding segment of the three-dimensional polygonal structure calculated previously. The diameters of the major and minor bases are found by processing the two-dimensional thicknesses (FIGS. 9 and 10) as indicated above.

The algorithms and procedures described above can be applied to images obtained by means of a single source and a single image intensifier, with a device of the type illustrated in FIG. 1. However, it is particularly useful to have an angiograph which has three sources of radiation and three image intensifiers, carried on corresponding arms which can be oriented. A possible configuration of an angiograph equipped in this way is shown in FIG. 12. In this figure, 1A, 1B, 1C indicate the three X-ray sources and 5A, 5B, 5C indicate three corresponding image intensifiers. The source 1A and the intensifier 5A are held by an arm 6A fitted in a support 8A which can be oriented about a horizontal shaft held by a pillar 14. A support 8C, similar to the support 8A, for the arm 6C which holds the source 1C and the image intensifier 5C can be oriented about the same horizontal shaft. The source 1B and the image intensifier 5B are carried on an arm 6B fixed to a support 8B which can be oriented and which can oscillate about a horizontal shaft carried by a pillar 16.

The number 7 again indicates the bed for the patient and 9A indicates the transparent panel on which the radiopaque points are disposed (see FIG. 3). The panel 9B is underneath the bed 7 and is not visible in FIG. 12.

The three arms 6A, 6B, 6C can oscillate about the two horizontal shafts, thus changing their positions. FIG. 12A shows the same apparatus as that in FIG. 12, with the arms in a different position.

Figure 13:
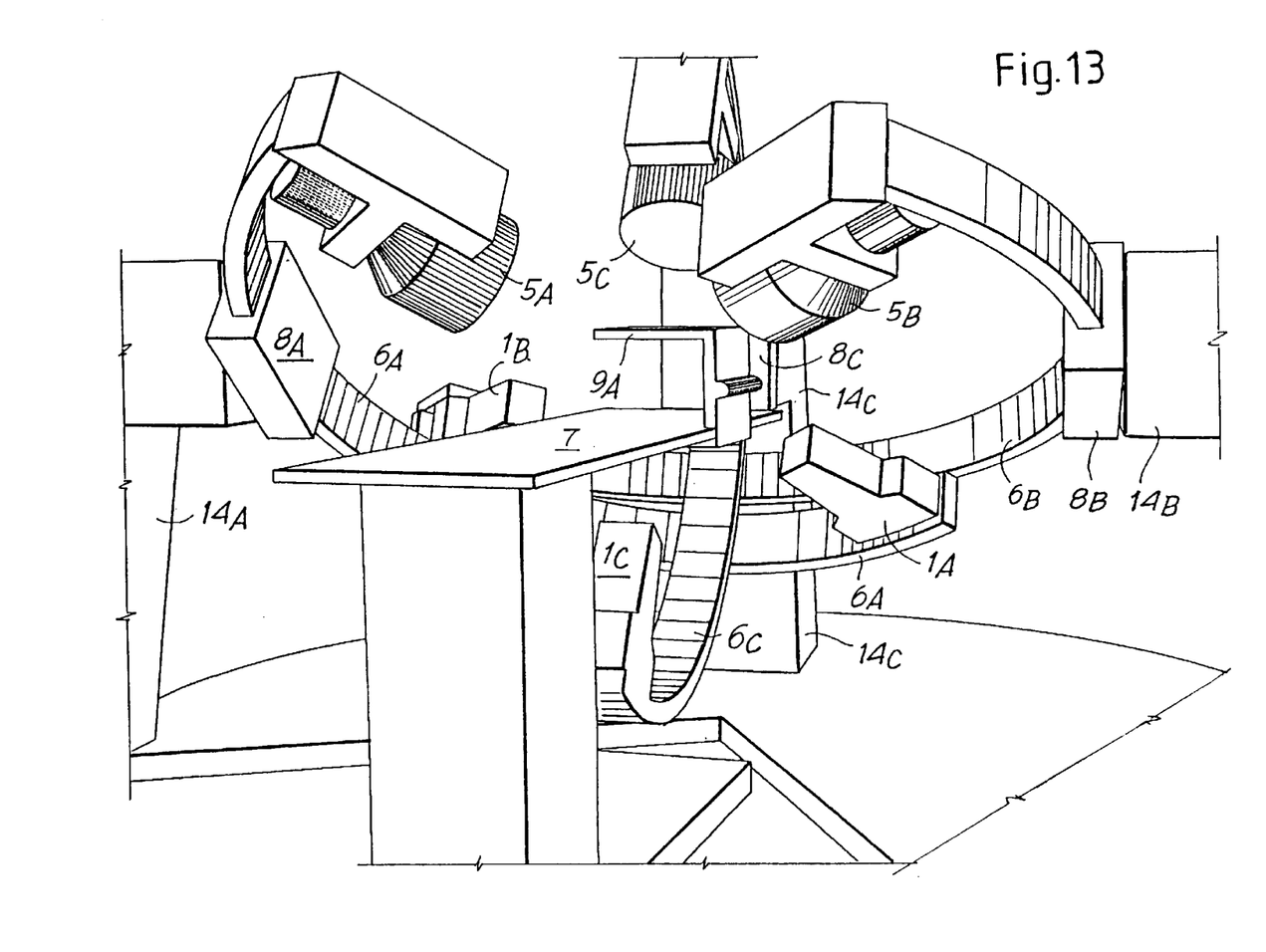
FIG. 13 shows a different configuration of a three-arm coronary angiograph.

FIG. 13 also shows an angiograph with three sources and three intensifiers. Identical numbers indicate parts that are identical to or correspond to those in FIG. 12. In this case, the three arms 6A, 6B, 6C are carried by supports 8A, 8B, 8C, each carried by a corresponding pillar 14A, 14B, 14C and each capable of being oriented about a horizontal shaft. The supports 8A, 8C can be oriented independently of each other about a common geometrical axis.

Figure 14:
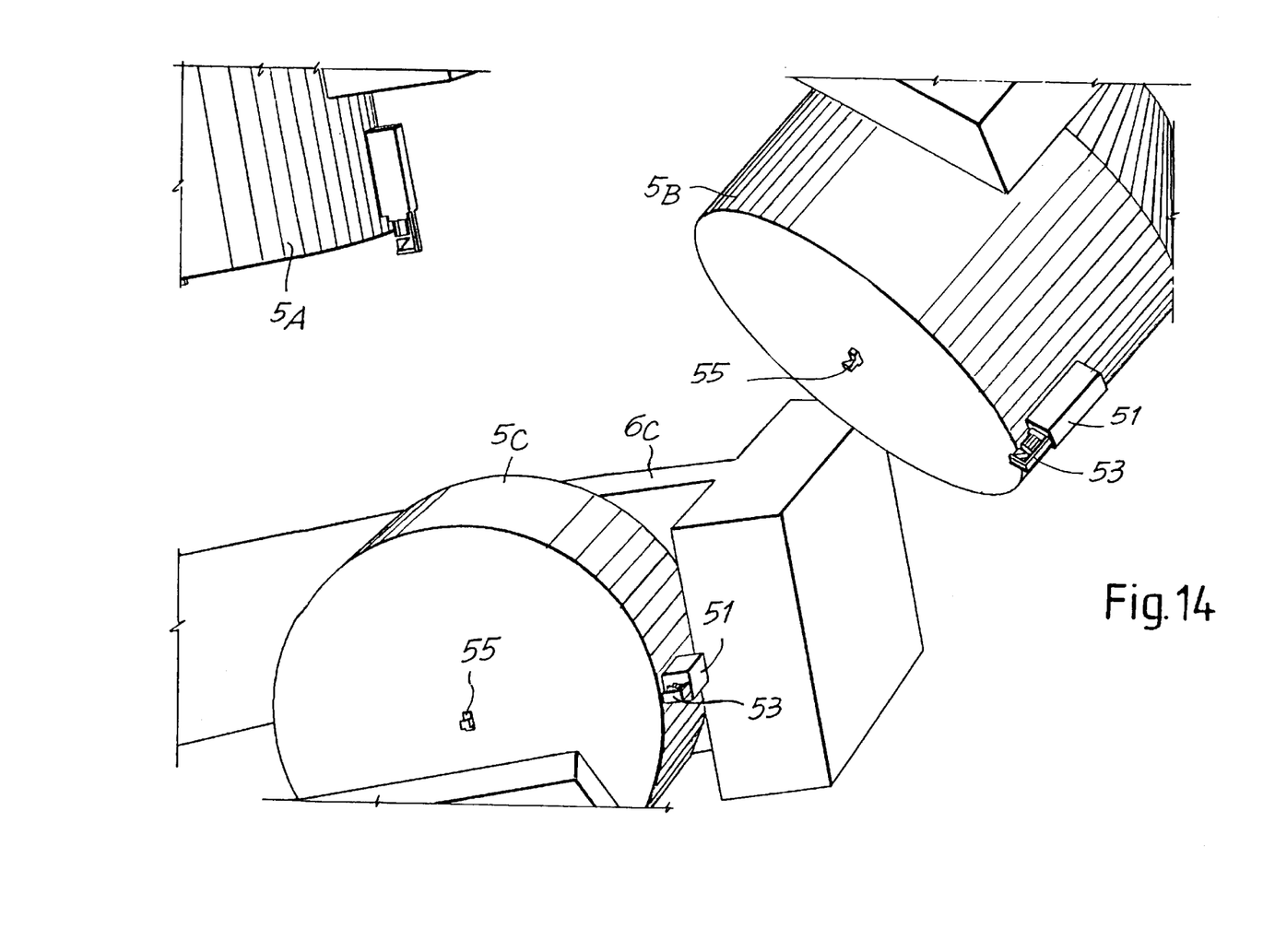
FIG. 14 shows an enlargement of the image intensifier with a laser aiming system.

Regardless of the configuration of the angiograph, the oscillating arm or each oscillating arm carrying a source and intensifier combination can be associated with a laser aiming system which facilitates the positioning of the source and of the intensifier with respect to the patient's body. This simplifies the aiming and positioning operations, thus reducing the periods of exposure of the patient to the radiation. A possible arrangement of the laser aiming system is shown schematically in FIG. 12 and in the enlargement in FIG. 14. The image intensifier (or each image intensifier) is associated with a small laser source 51 whose power and wavelength are such that they do not cause harm to the patient. The beam leaving the source 51 is deflected through 90° by a first deflecting optical element 53 located on the output axis of the optical beam. In this way, the deflected beam is directed toward the optical axis of the intensifier and is made to strike a second deflecting optical element 55 located on the axis of the image intensifier. This second optical element 55 is transparent to the X-rays, so that it does not impede the acquisition of the image by the intensifier. It also enables the laser beam from the source 51 to be directed toward the patient along the axis of the source-intensifier system.

This aiming system can also be associated with other types of medical or analytical apparatus in which it is necessary to carry out an aiming operation before switching on the radiation source for the acquisition of the image of a patient or an object.

Figure 15:
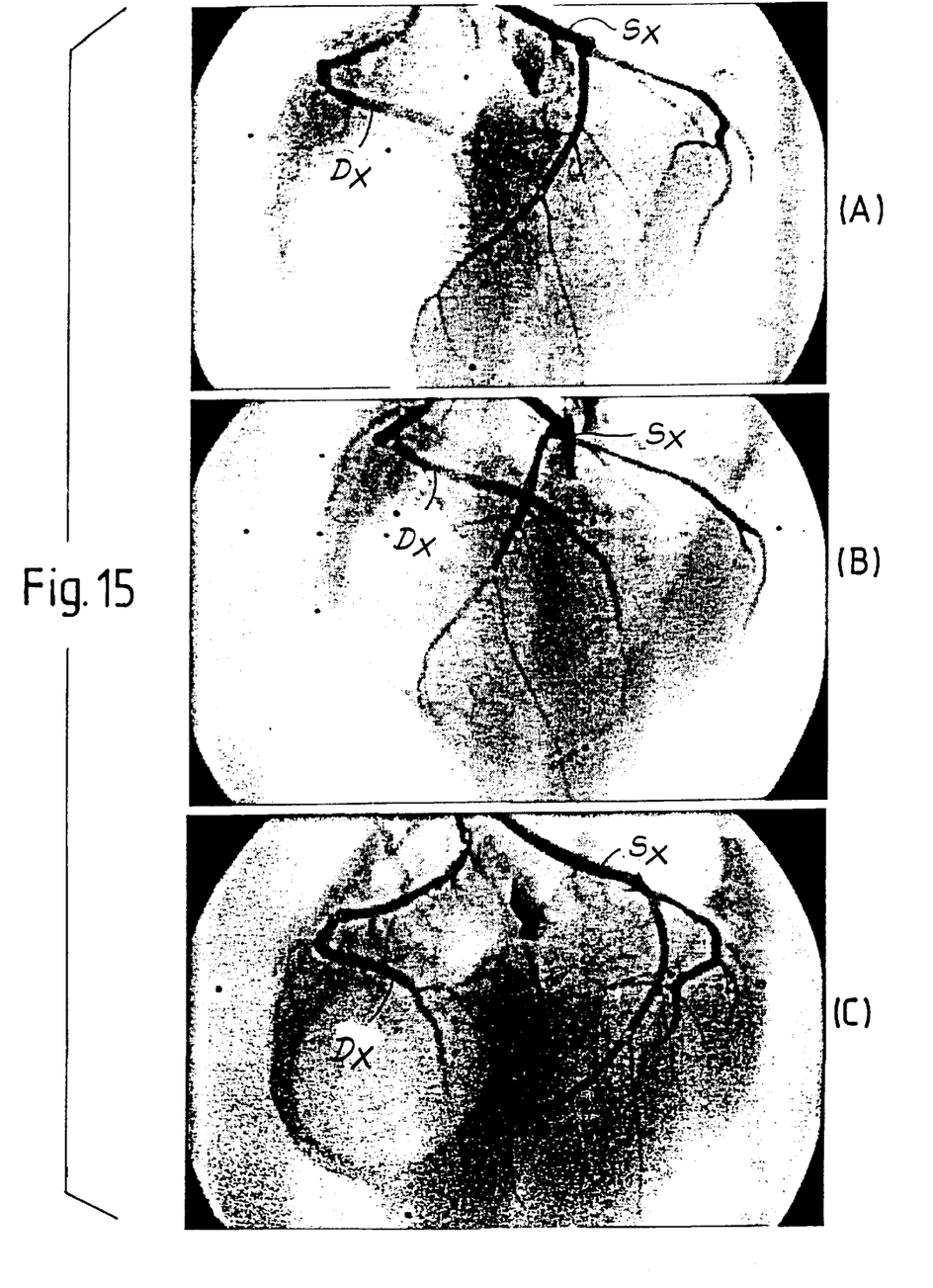
FIGS. 15 and 16 show experimental results obtained in vitro.
Figure 16:
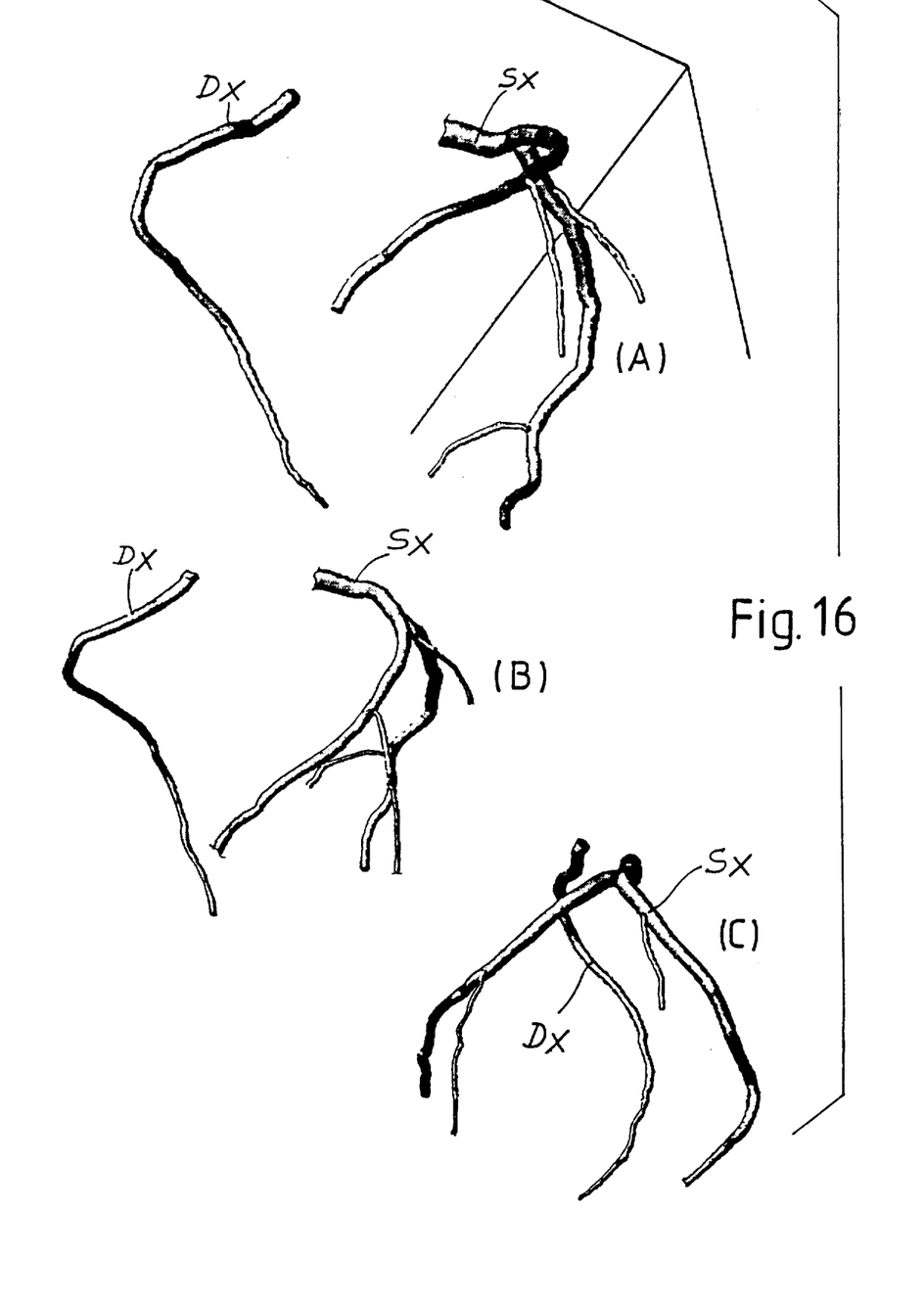

FIGS. 15 and 16 show the experimental results obtained with the method described above on a pig's heart in vitro. FIGS. 15(A), 15(B) and 15(C) show the three initial two-dimensional images of the heart. In these, Sx and Dx indicate the right-hand and left-hand coronary arteries. The reference points consisting of the radiopaque objects 10A–10E, 12A–12E are also visible. FIGS. 16(A), 16(B) and 16(C) show the three-dimensional image reconstructed by the described method. The references Sx and Dx are shown again.

It is to be understood that the drawing shows only an example provided solely as a practical demonstration of the invention, and that this invention may be varied in its forms and dispositions without departure from the guiding concept of the invention. The presence of any reference numbers in the attached claims has the purpose of facilitating the reading of the claims with reference to the description and to the drawing, and does not limit the scope of protection represented by the claims.

We claim:

1. A method for reconstructing a structure having a three-dimensional extension, comprising the stages of:

obtaining at least three images of the structure to be reconstructed, each of said images showing reference points which permit the determination of a matrix (T) which describes the geometric projections associated with each image;

identifying, by means of said three images, a starting point for the tracing of a center line of an elongate element of said structure;

tracking the center line of the elongate element to an end point;

determining the cross-sectional dimension of said elongate element at a plurality of points of the center line;

reconstructing the three-dimensional image of the elongate element from said cross-sectional dimensions and said center line.

2. The method as claimed in claim 1, in which the starting point for tracing the elongate element is identified by the following stages: defining a first point (P) on a first of said three images, lying on the center line of the elongate element; selecting, on a second of said three images, a second point (P') which is approximately the projection on said second image of the point identified in the first image; determining the three-dimensional point of which said first and said second points represent the projection on the first and second images; determining on the third image a third point (P") which is the projection of said three-dimensional point on said third image; checking that said third point on said third image lies approximately on the center line of the elongate element; and, if necessary, modifying the projection of the three-dimensional point on the second view until said third point is approximately on the center line of the elongate element in said third view.

3. The method as claimed in claim 2, in which the center line of the elongate element is followed in said first image by means of an algorithm comprising the following stages:

a) setting the starting point ($P_{i-1}$) and the initial reference direction by means of the vector ($d_i$);

b) determining the initial scanning radius and the initial thickness ($h_i$) by the formula:

$$r_i = |d_i|; \quad h_i = |d_i|/2$$

c) constructing an elongate geometrical figure having specified dimensions;

d) placing an end point of said elongate geometrical figure at the terminal point of the vector representing the initial direction ($d_i$);

e) rotating the elongate figure in steps through 180° about the center of rotation represented by the terminal point of said vector;

f) in each step of said rotation, determining the gray levels underlying the elongate figure belonging to he angiographic image and storing the corresponding mean value and angle of rotation ($\beta_i[k]$), generating a vector of angular values ($\beta_i$;

g) generating a vector ($l_i$) of means of the gray levels, containing the means of the gray levels found for each direction examined during said rotation;

h) calculating the maximum value ($l_{i\ max}$) and the mean value ($l_{i\ mean}$) of the values of said vector ($l_i$) of gray means;

i) initializing a threshold ($s_i$) proportional to said maximum values ($l_{i\ max}$) and mean ($l_{i\ mean}$);

j) starting from the position of the maximum value ($k_{max}$), determining the directions ($k_s$) and ($k_d$) relative to the mean values immediately below the set threshold ($s_i$) and on the left and on the right respectively;

k) calculating a direction ($k^1$) as a mean value between said right and left directions, the angle associated with the direction ($k^1$) representing the direction of the center line of the elongate element;

l) iterating the algorithm from point c).

4. The method as claimed in claim 1, in which the center line of the elongate element is followed in said first image by means of an algorithm comprising the following stages:

a) setting the starting point ($P_{i-1}$) and the initial reference direction by means of the vector ($d_i$);

b) determining the initial scanning radius and the initial thickness ($h_i$) by the formula:

$$r_i=|d_i|;\ h_i=|d_i|/2$$

c) constructing an elongate geometrical figure having specified dimensions;

d) placing an end point of said elongate geometrical figure at the terminal point of the vector representing the initial direction ($d_i$);

e) rotating the elongate figure in steps through 180° about the center of rotation represented by the terminal point of said vector;

f) in each step of said rotation, determining the gray levels underlying the elongate figure belonging to he angiographic image and storing the corresponding mean value and angle of rotation ($\beta_i[k]$), generating a vector of angular values ($\beta_i$;

g) generating a vector ($l_i$) of means of the gray levels, containing the means of the gray levels found for each direction examined during said rotation;

h) calculating the maximum value ($l_{i\ max}$) and the mean value ($l_{i\ mean}$) of the values of said vector ($l_i$) of gray means;

i) initializing a threshold ($s_i$) proportional to said maximum values ($l_{i\ max}$) and mean ($l_{i\ mean}$);

j) starting from the position of the maximum value ($k_{max}$), determining the directions ($k_s$) and ($k_d$) relative to the mean values immediately below the set threshold ($s_i$) and on the left and on the right respectively;

k) calculating a direction ($k^1$) as a mean value between said right and left directions, the angle associated with the direction ($k^1$) representing the direction of the center line of the elongate element;

l) iterating the algorithm from point c).

5. The method as claimed in claim 4, in which said elongate geometrical figure is a rectangle.

6. The method as claimed in claim 5, in which said rectangle has sides equal to the scanning radius ($r_i$) and the thickness ($h_i$).

7. The method as claimed in claim 5, in which said estimated value of the scanning radius is determined by:

$$r_{i+1}=|k_{is}-k_{id}|*1.5$$

where $k_{is}$ and $k_{id}$ are the directions ($k_s$, $k_d$) corresponding to the mean values lying immediately below the set threshold ($s_i$) calculated in the preceding step.

8. The method as claimed in claim 4, in which in each step the scanning radius for the next iteration is determined as the arithmetic mean of the last three calculated values and a fourth estimated value.

9. The method as claimed in claim 4, in which in every i-th iteration a check is made to determine whether the difference $|k_s-k_d|$ is less than a specified fraction of that calculated during the preceding iteration, and, if this is so, the values obtained are rejected and the search for the next corresponding maximum is continued by continuing the scanning of the vector ($l_i$) of means of the gray levels.

10. The method as claimed in claim 1, in which, for each point of the center line of the elongate element identified on a first of said images, the straight line passing through said point, through the three-dimensional point of which said point is the projection on the first image, and through the source ($S_1$) which has generated the point of the center line on said first image is determined; said straight line, or a segment of it, is projected on said second and/or said third image; the resulting luminosity profile is analyzed by sampling the gray levels of the second and/or third image along the projection of said straight line or said segment of straight line; and the projection of the three-dimensional point on said second and/or third image is identified as the point of lowest luminosity along the projection of said straight line or said segment of straight line.

11. A device for reconstructing a three-dimensional structure, comprising: at least one source of radiation and a receiver for said radiation, the three-dimensional structure being located between said source and said receiver; an object (9) capable of being associated with the three-dimensional structure and carrying a plurality of radiopaque points; and means for obtaining at least three images at three different angles of a single three-dimensional structure.

12. The device as claimed in claim 11, in which said object comprises two panels (9A, 9B) transparent to the radiation of said source and applied to a bed (7) for a patient, said three-dimensional structure consisting of a group of blood vessels of said patient.

13. The device as claimed in claim 11, comprising three oscillating arms (6A, 6B, 6C), each of which carries a radiation source (1A, 1B, 1C) and a corresponding receiver (5A, 5B, 5C), said three arms being capable of being positioned independently of each other, for the simultaneous acquisition of three images at three different angles.

14. The device as claimed in claim 11, in which said receiver or said source is associated with a laser source (51) with optical deflector means (53, 55) which align the laser beam emitted by said source with the optical axis of the system formed by said radiation source and said receiver.

15. The device as claimed in claim 14, in which said optical deflector means comprise a first deflector element (53), located in the axis of the output of the laser source, which deflects the laser beam through 90° toward the optical axis of the system formed by the radiation source and the receiver, and a second deflector element (55), transparent to the radiation of said radiation source, positioned on the optical axis of said system.

16. The device as claimed in claim 14, in which said laser source and said optical deflector means are associated with the receiver.

17. The device as claimed in claim 11, comprising processing means for implementing the method as claimed in claim 1.

* * * * *